(12) United States Patent
Gonzalez Ulloa

(10) Patent No.: US 10,493,121 B2
(45) Date of Patent: Dec. 3, 2019

(54) METHOD FOR PROCESSING RAW SUGARCANE MAXIMIZING THE PRESERVATION OF POLICOSANOLS DURING PRODUCTION OF A NATURAL SUGARCANE JUICE-BASED PRODUCT

(71) Applicant: Jorge Enrique Gonzalez Ulloa, La Calera (CO)

(72) Inventor: Jorge Enrique Gonzalez Ulloa, La Calera (CO)

(73) Assignee: The Cane Juice Company, LLC, Jupiter, FL (US)

( * ) Notice: Subject to any disclaimer, the term of this patent is extended or adjusted under 35 U.S.C. 154(b) by 0 days.

(21) Appl. No.: 16/163,365

(22) Filed: Oct. 17, 2018

(65) Prior Publication Data

US 2019/0216876 A1    Jul. 18, 2019

Related U.S. Application Data

(63) Continuation-in-part of application No. 15/803,037, filed on Nov. 3, 2017.

(51) Int. Cl.
*A61K 36/899* (2006.01)
*A61K 31/045* (2006.01)
(Continued)

(52) U.S. Cl.
CPC .............. *A61K 36/899* (2013.01); *A23L 2/04* (2013.01); *A23L 2/72* (2013.01); *A23L 2/82* (2013.01);
(Continued)

(58) Field of Classification Search
CPC .................................................. A61K 36/899
(Continued)

(56) References Cited

U.S. PATENT DOCUMENTS 6,068,869 A    5/2000 Ginslov
6,245,153 B1 *    6/2001 Gonzales .............. C13B 30/002
127/30
(Continued)

OTHER PUBLICATIONS

Ogier et al., "LDL-cholesterol-lowering effect of a dietary supplement with plant extracts in subjects with moderate hypercholesterolemia" Eur J Nutr (2013) 52:547-557, DOI 10.1007/s00394-012-0357-x. Accepted: Apr. 3, 2012/Published on line: Apr. 24, 2012 copyright Springer-Verlag 2012.

(Continued)

*Primary Examiner* — Michael Barker
*Assistant Examiner* — Deborah A Davis
(74) *Attorney, Agent, or Firm* — Glenn E. Gold, P.A.; Glenn E. Gold

(57) ABSTRACT

A method for processing sugarcane juice from raw sugarcane stalks to produce various forms of a natural sugarcane juice product preserves policosanols naturally occurring in the raw sugarcane stalks, resulting in policosanol-rich natural sugarcane juice-based products such as a drinking beverage, a concentrated sweetening agent, and a nutraceutical product. The method may include steps of providing sugarcane stalks having high policosanol concentrations; extracting sugarcane juice from the sugarcane stalks via a series of roller mills; filtering the extracted sugarcane juice; stabilizing the pH of the juice in a non-acidic solution of calcium hydroxide; flocculating the sugarcane juice to remove undesirable impurities; optionally, evaporating the sugarcane juice to form a policosanol-rich sugarcane juice concentrate and extracting the sugarcane juice concentrate from the evaporator.

18 Claims, 7 Drawing Sheets

(51) Int. Cl.
*A23L 33/105* (2016.01)
*A23L 2/04* (2006.01)
*A23L 2/72* (2006.01)
*A23L 2/82* (2006.01)
*A61K 9/00* (2006.01)

(52) U.S. Cl.
CPC .......... *A23L 33/105* (2016.08); *A61K 9/0095* (2013.01); *A61K 31/045* (2013.01); *A23V 2002/00* (2013.01); *A61K 2236/15* (2013.01); *A61K 2236/333* (2013.01); *A61K 2236/39* (2013.01); *A61K 2236/51* (2013.01)

(58) Field of Classification Search
USPC ........................................................ 424/750
See application file for complete search history.

(56) References Cited

U.S. PATENT DOCUMENTS

| | | | |
|---|---|---|---|
| 7,931,784 | B2 | 4/2011 | Medoff |
| 8,828,142 | B2* | 9/2014 | Oliveira ............... C13B 5/02 127/44 |
| 2007/0121584 | A1 | 5/2007 | Qiu et al. |
| 2007/0248621 | A1 | 10/2007 | Lowther et al. |
| 2009/0126719 | A1 | 5/2009 | Almagro |
| 2016/0263177 | A1 | 9/2016 | Kannar et al. |

OTHER PUBLICATIONS

Gonzalez Ulloa, PCT-US18-58537, ISR-WO, Feb. 21, 2019, pp. 1-8.

* cited by examiner

METHOD FOR PROCESSING RAW SUGARCANE MAXIMIZING THE PRESERVATION OF POLICOSANOLS DURING PRODUCTION OF A NATURAL SUGARCANE JUICE-BASED PRODUCT

CROSS-REFERENCE TO RELATED APPLICATION(S)

This application is a continuation-in-part of U.S. patent application Ser. No. 15/803,037, filed Nov. 3, 2017, which is incorporated by reference herein in its entirety.

Field of the Invention

The present invention relates generally to sugarcane processing. More specifically, the invention pertains to large-scale commercial processing of raw sugarcane to produce shelf-stable natural sugarcane-based products for human consumption therefrom while maximizing the preservation of the raw sugarcane policosanols in the consumable products.

BACKGROUND OF THE INVENTION

The production of crystallized sugar from raw sugarcane is well known. Furthermore, the development of equipment and associated processes for producing sugar from sugarcane stalks has been extensive. Generally, sugar product is produced from a naturally occurring liquid contained within the cells of raw sugarcane stalks.

In many places throughout the world, and especially in Latin America, this naturally-occurring juice contained in the cells of sugarcane stalks is highly regarded as a beverage. In Latin America, this natural juice product is commonly referred to as "guarapo." The term "guarapo," which carries the unmistakable sonority of its Quechuan origin, has become part of the Spanish lexicon to identify and define arguably the most pleasant and truly popular beverage in South America, Fresh guarapo has long been regarded as a healthy beverage which, in addition to providing thirst-quenching refreshment, is believed to have attributes that improve and enhance sexual performance. In fact, songs mitten by grateful Latin Americans having firsthand knowledge of its gifts have become an integral part of Latin American folklore.

The present applicant, in his issued U.S. Pat. No. 6,245,153 (the entire contents of which are incorporated-by-reference herein) taught an improved method for processing raw sugarcane to produce a consumable sugarcane juice, which overcame significant shelf-life limitations of then state-of-the-art sugarcane processing methods. Prior to applicant's aforementioned patented invention, there were no known methods for efficiently producing a natural guarapo product having an adequate shelf life to support commercial distribution thereof. In his '153 patent, the present applicant teaches a novel method for producing a stabilized natural sugarcane juice product having an adequate shelf life to enable commercial distribution, without requiring addition of unnatural chemical additives, such as acids, during juice processing.

Since the time of applicant's initial invention (i.e. as disclosed in applicant's '153 patent), there has been a dramatic increase in the occurrence of dangerously high blood cholesterol levels in humans. In fact, the Centers for Disease Control and Prevention (i.e. the CDC) currently estimates that 73.5 million adults in the United States alone, or 31.7% of the adult population of the United States, have unhealthy low-density lipoprotein (LDL) cholesterol levels, which the medical community has well established cause a host of health-related problems in humans. Furthermore, the CDC has indicated that only 29.5% (i.e. less than one-third) of adults with high LDL cholesterol have the condition under control. People with high total cholesterol levels have approximately twice the risk of heart disease as people with ideal total cholesterol levels.

The pharmaceutical industry has addressed the high-cholesterol problem by continuing to develop a host of cholesterol-lowering drugs known as "statins," including those sold under the brand names LIPITOR, PRAVACHOLD, CRESTOR, ZOCOR, LESCOL and VYTORIN, to name just a few examples. Statins are a class of medicines that are used to lower blood cholesterol levels by blocking the action of an enzyme in the liver that is necessary for making cholesterol. Cholesterol is necessary for normal cell and body function, but above normal, or high, LDL and total cholesterol levels can lead to atherosclerosis, a condition in which cholesterol-containing plaques build up in the arteries and block blood flow. By reducing blood cholesterol levels, statins reduce the risk of chest pain (i.e. angina), heart attack, and stroke. However, there are numerous well-documented risks and side effects associated with such pharmaceutical statin drugs. Most people who take statins have undesirable side effects, including, but not limited to, headaches, pins-and-needles sensation, abdominal pain, bloating, diarrhea, nausea, and skin rashes. Furthermore, it has been found that some statin drugs may impair memory and increase the risk for development of cataracts, in addition to causing more serious side effects such as liver failure and skeletal muscle damage. Additionally, a significant segment of the high-cholesterol population is advised against taking statins, including people with progressive liver disease, and pregnant and breast-feeding women (or those intending to become pregnant).

Concurrently, there has been an increasing awareness throughout the medical community that policosanol, a naturally-occurring ingredient of raw sugarcane, has shown growing promise as an effective remedy for the treatment of unhealthy elevated blood cholesterol levels in humans. Researchers have found that policosanols contained in raw sugarcane stalks are remarkably effective and very safe for reducing levels of low-density lipoprotein (LDL), a component of cholesterol that is known to cause a host of health-related problems at elevated levels in individuals. While policosanol is a naturally-occurring component of sugarcane, chemically speaking, it is completely unrelated to sugar. Sugar and policosanol just happen to come from the same plant. The effectiveness of policosanol in the treatment of high cholesterol levels has proven to be so remarkable that initial estimates of the recommended daily intake of policosanol required to efficiently and effectively reduce above-normal LDL and total cholesterol levels is miniscule.

Policosanol is a type of alcohol. More particularly, "policosanol" is the collective name referring to a group of related solid alcohols (i.e. long-chain primary aliphatic saturated alcohols). Policosanol is known to improve blood lipids, and research studies documenting its highly beneficial effects on human cholesterol levels are continually being published. Medical research and studies have proven that policosanol reduces low-density lipoprotein (LDL)—commonly referred to as "bad cholesterol"—while simultaneously increasing high-density lipoprotein (HDL)—commonly referred to as "good cholesterol." Additional benefits of policosanol in the treatment of high cholesterol and a host of other health-related issues, as well as an in-depth description of how policosanol functions to provide such incredible health benefits, may be found, for example, in an Internet article available at www.life-enhancement.com/magazine/article/710-policosanol-improves-every-meastures-of-blood-cholesterol) and entitled: *Policosanol Improves Every Measure of Blood Cholesterol*, the entire contents of which are incorporated-by-reference herein. Ongoing medical and scientific research and corresponding studies strongly suggest that policosanol is more highly effective than synthetically-derived pharmaceuticals for treating high blood pressure. Furthermore, a particular policosanol compound, known as "octacosanol," has been found to provide additional health benefits, including treating insomnia caused by stress, improving athletic performance, and treating symptoms of Parkinson's disease, in addition to having anti-cancer properties (e.g., reduced/slowed tumor growth).

Significantly, octacosanol is the most prevalent policosanol component occurring naturally in epicuticular sugarcane stalk wax. Policosanol is a mixture of essential alcohols isolated from sugarcane wax (*Saccharum officinarum* L.) that consists of different components, with octacosanol representing 66% almost two-thirds) of such policosanol components.

Consequently, the ability to efficiently and effectively process a variety of highly-stable sugarcane juice products for human consumption while maximizing the preservation of policosanols in the raw sugarcane being processed has the potential to provide a means of enabling individuals with high cholesterol levels to consume such a small daily quantity of such a product that the respective corresponding sugar intake would be well within the maximum sugar intake recommended by the World Health Organization (WHO), which has recommended a maximum daily sugar intake for adults of five percent (5%) of total daily caloric intake. For a normal weight adult, that is about 25 grams of sugar per day.

Unfortunately, the development of an efficient, repeatable, cost-effective commercial method for maximizing the extraction of policosanols from raw sugarcane during production of a stable natural consumable sugarcane juice product has proven elusive. Accordingly, there has been a long felt, yet unmet, need for a repeatable, reliable, and cost-effective method of processing raw sugarcane to produce a highly stable policosanol-rich consumable sugarcane juice product on a commercial scale. Such a method would provide a means for producing a natural cholesterol-lowering consumable product at such a low cost that it could be made readily available to all individuals; particularly, the millions of people that currently do not have the financial means to afford existing pharmaceutical drugs. Furthermore, such a method would provide a healthy alternative to drugs manufactured by the pharmaceutical industry that are known to have negative health side effects.

Accordingly, applicant began experimenting with alternative sugarcane processing methods for producing a variant of his stabilized sugarcane juice product, which maximizes the preservation of the policosanols naturally stored in the cells of the pre-processed raw sugarcane used to produce his shelf stable sugarcane juice. Following extensive research and experimentation, applicant has discovered a variation of the sugarcane processing method originally disclosed in his above-identified issued (U.S. Pat. No. 6,245,153), which overcomes the aforementioned challenges by providing a repeatable, efficient, and highly cost-effective process for the commercial production of a policosanol-rich, stable, consumable product from raw sugarcane. Furthermore, applicant's process enables the production of such policosanol-rich, stable, consumable products in a variety of forms including, for example, a ready-to-drink (i.e. potable) juice beverage, a concentrate that can be used as a sweetener to be added to an existing beverage, and a highly-concentrated nutraceutical, to name just a few.

SUMMARY OF THE INVENTION

The present invention relates to a method for processing a shelf stable sugarcane juice product from raw sugarcane, which preserves naturally-occurring policosanols found in raw sugarcane, as well as to the products produced by the inventive method. The method incorporates a sugarcane juice extraction process that preserves the natural flavor of the juice, prevents natural fermentation of the processed juice and preserves the natural color of the juice. Furthermore, the method enables the bottling and long-term storage of a variety of forms of policosanol-rich sugarcane juice products, and has been adapted for producing large volumes of juice product, in a variety of forms, for large-scale commercial production and distribution.

These and other objects are achieved by the method of the present invention. In a general exemplary implementation of the method, sugarcane juice is extracted from manually-harvested high sucrose content sugarcane sticks using a roller mill tandem. Juice extracted from the mills is filtered and then stabilized at a pH of about 7.4 to 7.6 through the addition of Calcium Hydroxide. Subsequently, the juice product may be heated from a temperature in the range of about 20° C. to 30° C., to a temperature not exceeding 90° C. Subsequently, the juice product may be subjected to a series of clarification processes in which natural or industrial additives may be. Subsequently, the juice product may be concentrated through an evaporation step to form a sugarcane juice concentrate. Subsequently, the concentrate may be further clarified and further concentrated to a Brix of about 75+/−5 degrees.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, in which.

DETAILED DESCRIPTION OF EXEMPLARY IMPLEMENTATIONS

The following detailed description is merely exemplary in nature and is not intended to limit the described embodiments or the application and uses of the described embodiments. As used herein, the word "exemplary" or "illustrative" means "serving as an example, instance, or illustration," Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
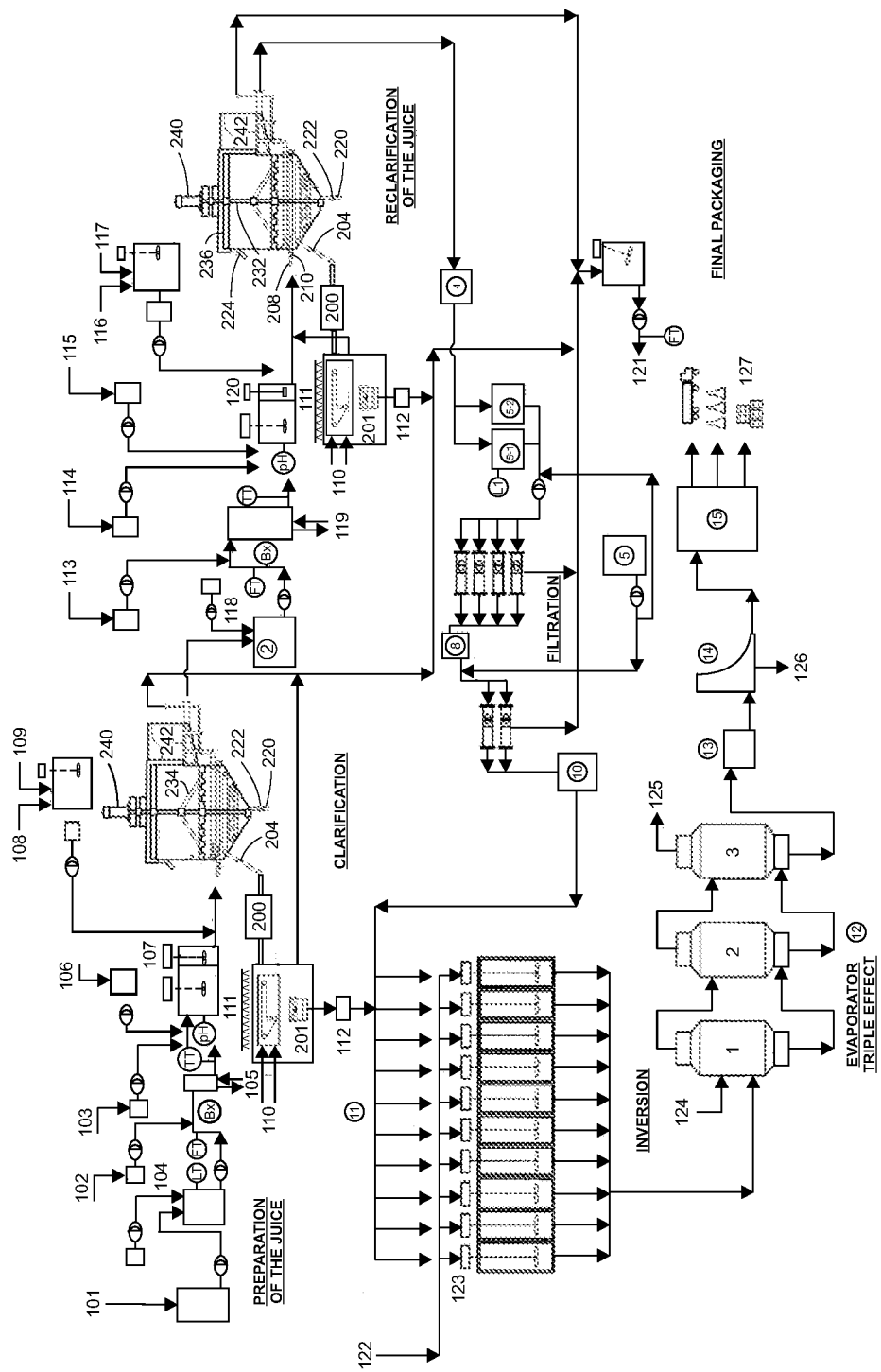
FIG. 1 is a schematic illustration of an exemplary implementation of a method for producing a consumable policosanol-rich sugarcane product, in accordance with the present invention.
Figure 2:
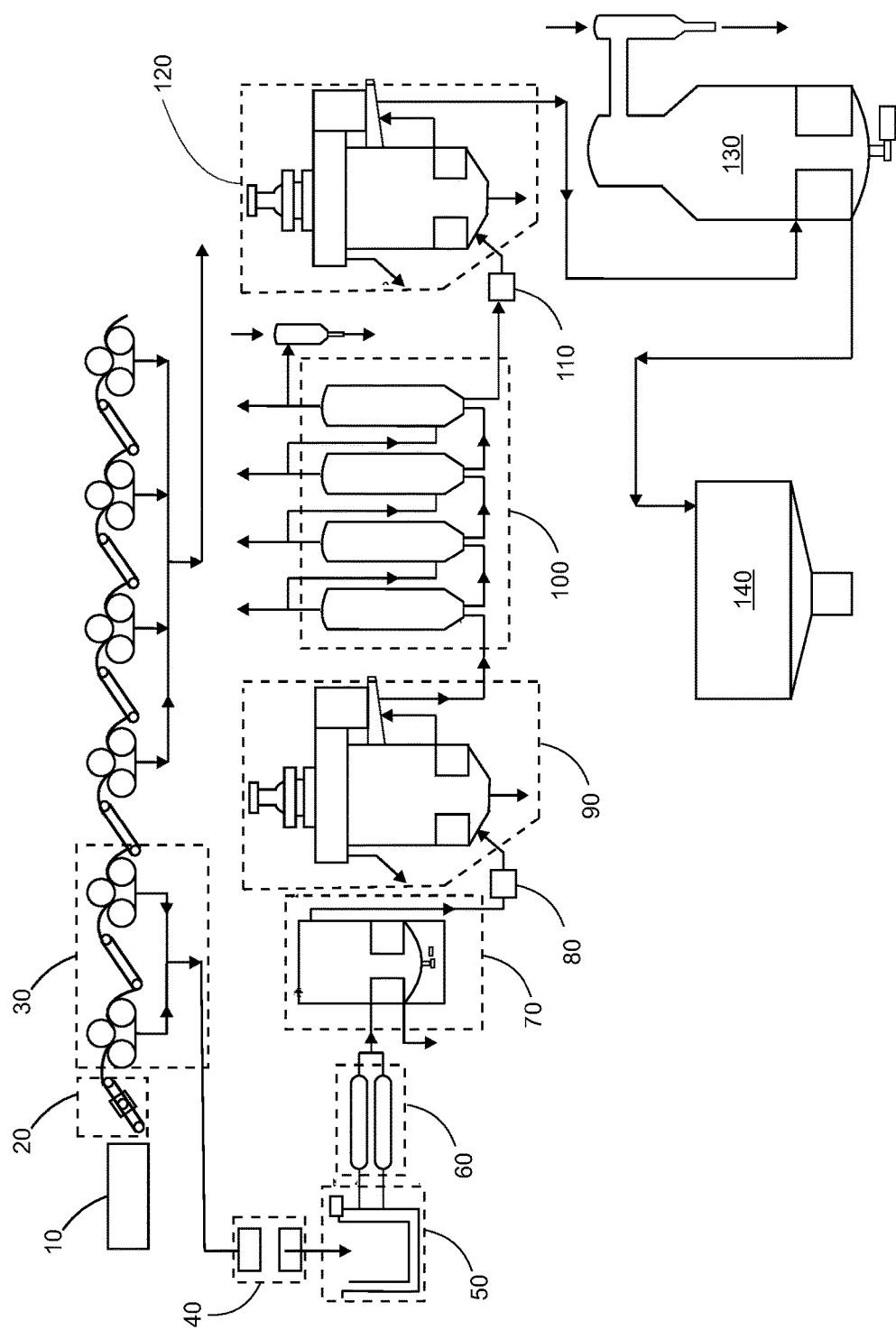
FIG. 2 is a schematic illustration of a sugarcane juice clarifying apparatus that may be employed with the method of the present invention.
Figure 3:
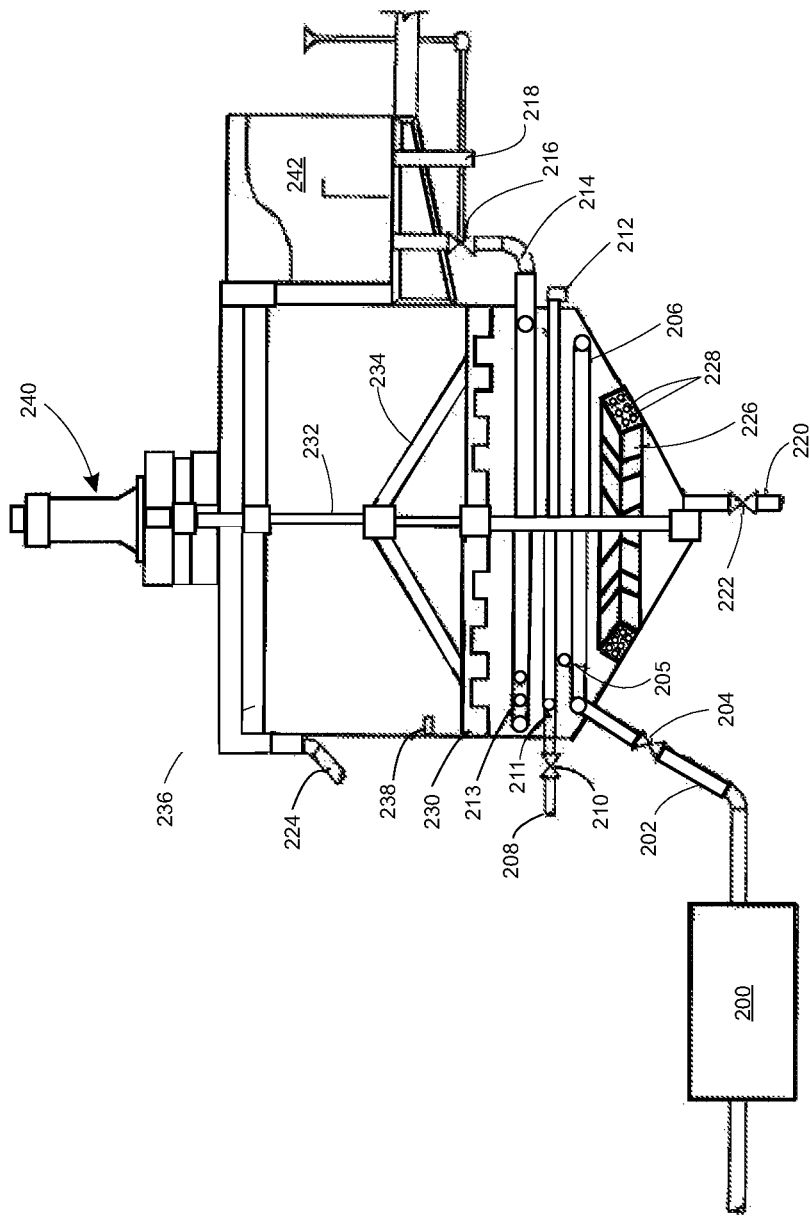
FIG. 3 is a schematic illustration of an apparatus that may be used during juice clarification sub-steps of the process.

Referring now to FIGS. 1-3, the method of the present invention generally includes the following steps:

Sugarcane Selection:

Initially, it is preferable to select extremely sweet, soft and flavorful varieties of sugarcane which have substantially no acidic content. In particular, it is preferred that the raw sugarcane chosen for processing yields a Brix within a range of 18 to 28 degrees Brix. It will be apparent to those skilled in the art of sugarcane processing, that numerous varieties of sugarcane meeting the preferred standards are available in various regions of the world. Well known examples of sugarcane varieties which work well with the process of the present invention include: CCSP2000 CENICANA COLOMBIA SAO PAOLO; CC8568 CENICANA COLOMBIA; CC8592 CENICANA COLOMBIA; MY74275 MAYAGUEZ; CCSP1940 and POJ2878, to name just a few.

Sugarcane Harvesting & Transport:

In the majority of sugar mills around the world, burning the standing sugarcane to facilitate cutting and lifting for transport to the mill is common practice. Where mechanical harvesting is employed and equipment is used for both cutting and lifting, the step of burning is not required. Unfortunately, sugarcane burning introduces ash byproduct which alters the natural flavor of the sugarcane juice; however, burning is not required and can be eliminated. Consequently, in the method of the instant invention it is absolutely imperative to avoid the step of burning, since this conventionally used step evaporates policosanols and a primary purpose of the present method is the retention of such policosanols. Where mechanical harvesting is employed and equipment is used for both cutting and lifting, the flavor or the green leaves is bitter and the taste contaminates the juice and cannot be removed.

To avoid the need for sugarcane burning, it is preferred that the sugarcane chosen for use with the present invention is manually cut approximately two inches from the stool, removing all green and dry leaves. It is also preferable that the sugarcane tops, commonly referred to as "cogollos," are cut off; thereby avoiding the introduction of their pasty taste which is difficult to eliminate in processing without the use of chemical additives. It is crucial that the cut cane stalks are not cleaned at this step because the majority of policosanols in raw sugar cane are contained within the outer portion (or cortex) as a wax containing upwards of 80 percent (80%) of the policosanols. Furthermore, if the cane is burned then the policosanols are evaporated, completely defeating the purpose of the invention. As described further herein below, policosanol is extracted from the wax during subsequent rolling operations. Furthermore, for similar reasons, it is absolutely crucial that the temperature of the extracted product containing policosanols is never subjected to a temperature greater than 90° C. This is a crucial departure from conventional raw sugarcane processing, and would not occur to those skilled in the art since heretofore the preservation/retention of policosanols has not, prior to applicant's invention, been a consideration.

Once the sugarcane has been manually cut, the unwashed cut cane should be lifted into a vehicle for transportation to a processing facility. Avoiding mechanical harvesting provides the further benefit of avoiding the introduction of foreign matter commonly carried into the processing mill along with the sugarcane. The foreign matter, often comprising ten percent or more of the sugarcane weight, primarily consists of soil, sludge, ash, leaves, minerals and cane tops. The introduction of the aforementioned foreign matter has the undesirable effect of altering the natural flavor of subsequently extracted sugarcane juice.

Chopving & Juice Extraction:

The cut sugarcane stalks are initially transferred onto a conveyer table 10 (FIG. 2) where they remain unwashed. This is highly significant and very different than conventional sugarcane processing wherein sugarcane stalks are washed thoroughly for removal of impurities (without regard to removing the wax). Subsequently, the sugarcane stalks are conveyed through a standard chopping apparatus 20 to reduce the stalks into smaller individual pieces for feeding through a series of roller mills.

The sugarcane juice extracted at each of the mill sites, in the process of the present invention goes directly to the factory to be processed according to the invention. It is important that the cane is milled at the lowest possible rate. In particular, the milling rate is preferably reduced to approximately 50 percent of the rate used during conventional sugar production. This reduced rate allows the milling equipment to run without stress (i.e. since not at fill capacity) so the resulting product quality is maximized.

Conventional sugarcane juice extraction methods incorporate hot water maceration to aid in the extraction process. Thus, the sugarcane should be macerated with clean—preferably treated—hot water. For example, it is preferred that the water used for maceration have a temperature within a range of about 80 to 90 degrees Celsius.

Macro-Particle Filtration:

Initially, the sugarcane juice extracted 30 is subjected to a standard filtration process 40 for removing macro-sized particles from the juice product, as is well known in the industry. For the purpose of the present invention, the term macro-sized particle is used to denote particles having an average diameter on the order of at least approximately 1.0 to 1.5 microns. Preferably, macro-particle filtration is accomplished by passing the juice extracted through a standard steel screen filter having about 300-400 openings/in$^2$ followed by passage through a standard vibrating screen filter having 1.0 to 1.5 micron diameter holes and a vibration frequency of approximately 800 vibrations/minute.

Initial pH Stabilization:

Once the macro-sized particles have been substantially removed from the juice, the juice is subjected to a pH stabilization step 50. Precise pH control of the sugarcane juice is critical. The standard procedure in sugar mills is to add Calcium Hydroxide (CaOH), also referred to as milk of lime, until the pH level of the limed juice attains a value in the range of 8.0 to 8.5. With known sugarcane juice processes, the pH level of 8.0 to 8.5 is maintained prior to subjecting the juice to a clarification process, such that the resulting pH level is about 7.0 following clarification.

In the method of the present invention, the quantity of Calcium Hydroxide added to the sugarcane juice is limited to an amount required to achieve a pH level within a range of about 7.4 to 7.6 and preferably about 7.5. Consequently, the quantity of Calcium Hydroxide additive is reduced relative to the quantity typically introduced using existing processes. This reduction is critical for maintaining the natural flavor of the sugarcane juice and the policosanol. In general, retaining the natural flavor of the sugarcane juice in the final product requires minimizing the quantity of juice additives such as Calcium Hydroxide during processing. Following the subsequently performed steps of heating 60 and clarification 70, the resulting pH level of the sugarcane juice product is maintained at approximately 7.2 to 7.6; optimal for retaining the natural flavors.

Heating:

Following the step of pH stabilization, the juice product is heated 60 from an initial temperature of approximately 26.7 to 29.4° C., to a temperature of approximately 80° C. to 90° C.; however, in the present case it is crucial that the temperature never exceeds 95° C. in order to prevent the loss of policosanols. Heating may be accomplished using a standard heating apparatus as is well known in the industry. For example, one well known type of juice heating apparatus adequate for use with the process of the present invention comprises a vertical or horizontally disposed steel cylinder having plates at opposite ends for supporting juice-communicating tubes there between. The flow of juice through the series of tubes is controlled by a series of baffles. Low pressure steam is communicated into the cylinder through a series of mechanical valves and connectors, arranged such that the steam is flowed through a specific path, minimizing the formation of non-condensable gas pockets. The condensate is typically extracted from a lower part of the cylinder via a steam trap.

Initial Standard Clarification:

Following the step of heating, the limed juice product is communicated to a standard clarification apparatus 70, as is well known in the industry. Significantly, as further described below, the present method deviates from the method described in applicant's previous process (i.e. U.S. Pat. No. 6,245,153) in that, for example, the Cachaza was discarded during the prior process. In the present method, the Cachaza is retained because it contains a concentration of policosanols to be preserved during the present process. Standard clarification includes the addition of any of a number of commonly-used industrial flocculates. For instance, CALGON CANE FLOC R-200 and STORKHAUSEN PRAESTOL are two examples of well-known industrial flocculates used for clarification. The flocculates attach to impurities in the limed juice and then descend to the bottom of the clarifying apparatus. With known processes, the Cachaza is extracted through standard froth pumps, filtered using a standard filter such as an Oliver filter, and transferred into storage tanks for subsequent use in raw sugar production. However, in the process of the present invention the juice obtained following froth pump filtration requires further purification to retain the natural flavor of the sugarcane juice.

With regard to known extraction processes, a quantity of non-sugar impurities is retained in the juice. The following table illustrates the non-removed impurities present in the juice following standard filtration:

TABLE 1

Impurities requiring additional filtration

| | (mg/l) |
|---|---|
| Organic Non-Sugars | |
| Waxy materials (total) | 300-800 |
| Waxy materials; hard sugarcane wax | 20-50 |
| Waxy materials; soft sugarcane wax | 50-100 |
| Waxy material; phosphates | 5-15 |
| Total Proteins | 15-100 |
| Gums | 5-50 |
| Inorganic Non-Sugar Cations | |
| CaO | 100-500 |
| MgO | 10-80 |
| $Fe_2O_3$ | 5-30 |
| $Al_2O_3$ | 3-20 |
| Organic Components | |
| Waxy materials | 5-15 |
| Protein non-sugars | 8-15 |
| Pentosans | 3-10 |
| Inorganic Components | |
| CaO | 1-5 |
| MgO | 1-5 |
| $Fe_2O_3/Al_2O_3$ | 3-10 |
| $P_2O_5$ | 1-3 |
| $SiO_2$ | 1-2 |
| Ash insoluble in Hydrochloric acid (clay & sand) | 5-20 |
| Very fine fiber ("bagacillo") | 15-150 |

Second Clarification:

In a second clarifying step 90, further clarification is accomplished using a novel clarifying apparatus to remove the majority of remaining non-sugar impurities in the limed juice. The general structure of the novel clarifying apparatus, designed for use with the process of the present invention, is explained in more detail below.

Natural agricultural flocculate or industrial flocculate is diluted with water and then added to the juice product in the novel clarifying apparatus. Examples of natural flocculates that can be used include: GUASIMO (GUAZUMA ULMIFOLIA LAMARK); BALSO (OCHOMA LAGOPUS SW); and CADILLO (TRIUMEETTA LAPPULA L). A natural flocculate would be used to obtain an organic cane juice concentrate.

Prior to being diluted, the natural flocculate is dried and ground into a fine powder. Preferably, the powdered flocculate is diluted with water to form a flocculate compound sufficient for removing remaining impurities in the juice. For example, Applicant has found success mixing 225 grams of any of the above natural flocculates in a tank holding 100 gallons of water. The flocculate mixture is subsequently injected 80 along with the juice into the clarifying apparatus. Applicant has found that 10 grams of flocculate per metric ton of juice provides adequate flocculation. The use of natural flocculates helps maintain the natural flavor of the sugarcane juice. The flocculate mixture combines with the remaining solids and other impurities suspended in the juice to form a glutinous froth, commonly referred to as Cachaza, which floats to the surface of the juice for easy separation.

Significantly, with the present process the Cachaza is not discarded because it contains a concentration of policosanols that are desired to be retained and preserved in the final product. The Cachaza is communicated to special clarifiers for further processing. In particular, the Cachaza is subjected to a vacuum press filtration process using a vacuum belt filter press, such as that the TECHNOPULP Vacuum Press Filter model VPB260 manufactured by Cordoba. Filtration Technologies of Ribeirao Preto, Sao Paulo, Brazil. An industrial filter press is a tool used in separation processes, specifically to separate solids and liquids. The process uses the principal of pressure drive, as provided by a slurry pump. A more in depth description of the operation and function of such a vacuum filter press may be found in the technical paper TRIALLING A TECHNOPUMP BELT PRESS FILTER AT PIONEER MILL (Prot Aust Soc Sugar Cane Technol Vol 25 2013), the entire contents of which are incorporated-by-reference herein.

Normally, the process can be carried out using any of a variety of commercially-available industrial flocculates, including, but not limited to: TALOFLOTE, manufactured by Tate & Lyle, Incorporated; PCS 3106, manufactured by Midland Research Labs; and QUEMIFLOC 900, AFI 1000, AP 273, TB 2634, VH 1007, QUEMICLAR QUEMIIFLOC 724, AH 1010, MPM 1032, and QUEMIFLOC SE, all manufactured by Quemi International, Incorporated. Furthermore, clarification can be carried out using any of a number of commercially available anionic and cationic flocculates.

Referring briefly to FIG. 2, the limed juice and flocculate mixture is injected into the bottom portion of the clarifying tank via conduit 202 controlled by valve 204. Subsequently, the mixture is directed into the tank through conduit extensions 205 an angle of approximately 45 degrees to effect circular rotation of the juice mixture in the tank. The lower section of the tank is provided with a steam coil 226 having a plurality of openings, preferably ⅛ inch (3.17 mm) in diameter, extending therethrough. The rate at which the steam is released should be just adequate to maintain a juice temperature of approximately 70° C. (but never exceeding 90° C.) and provide heat aeration to the juice to affect flocculate formation and flotation to the surface.

A bubble generating apparatus 208 is provided for enhancing the elevation of froth to the surface of the juice. The bubble generator has a vapor inlet 208 and valve 210 for controlling the flow of vapor into the generator. Vapor is released through openings 211 in the generator. A trap 220 is provided at the bottom of the tank for collecting heavy solids that are not carried to the surface. The trap is also used to empty the clarifying apparatus for cleaning.

Upper and lower sets of paddles, 236 and 230, respectively, are rotated at a rate of approximately 0.5 rotations per minute (rpm), by motor assembly 240. The lower paddles 230 produce a mild stirring motion which serves to gently stir the juice and effect flocculate formation. Impurity-rich foam froth is formed at the juice surface where it is subsequently, skimmed by upper paddles 236 for removal through slurry conduit 224. Preferably, the upper paddles are provided with curved or bowed surfaces to force the froth over the blades. Purified juice product is received through openings 213 in conduit 214 for transport into overfill tank 242. The purified juice is subsequently communicated through conduit 218 for further processing.

Evaporation & Extraction:

Following clarification step 90, the juice product is subject to the step of evaporation 100. The juice product is transferred to an evaporation apparatus through a transfer conduit. A series of sugar mill evaporators are employed to incrementally increase the sugarcane juice concentration. Preferably the juice concentrate is subsequently extracted from the evaporators at a Brix of about 60 degrees. Although a significantly higher Brix is possible, this is the preferred Brix for the additional clarification step 120.

As used herein, the term degrees Brix, represented by the symbol ° bx (and alternatively referred to herein simply as "degrees") is used to quantify the sugar content of an aqueous solution. More specifically, it is a relative density scale used in the sugar industry to indicate the percentage (%) of cane sugar (sucrose) by weight (i.e. grains of sucrose per 100 milliliters (ml) of solution). After clarification, the clarified juice is passed to the evaporators to obtain the syrup with a degrees Brix (° Bx) value of 55° Bx (+/−5° Bx). It is critical that during the evaporation step the solution never exceeds 70° Bx, in order to preserve the aforementioned policosanols.

The resulting syrup should have a pH in the range of about 6.0 to 6.4, and its color, if the prior steps were followed precisely, should not be more than 4500 IU The measurement of sugar color is an important function of the laboratories of sugar refineries and raw sugar mills, and is also for users of refined sugar products. For example, the ATM X2 COLORIVETER, manufactured by Index Instruments Limited of Cambridgeshire, England is an instrument dedicated to this important quality control function. International Commission for Uniform Methods of Sugar Analysis (ICUMSA) recommend the use of 420 nm as the wavelength for color measurements of white and light colored products, and a wave length of 560 nanometers (nm) for darker sugars. The result is displayed in ICUMSA Color Units (IU) at the wavelength selected. The different types of flocculants should preferably be about double the amount normally used during conventional sugar cane processing. In particular, it is preferred that the amount of flocculants used (e.g. TETRAFLOC) during this step is double the amount of the instructions, since it works better. It is also preferable that the flow of the clarifiers does not exceed 0.25 (or 25%) of the flow rate normally used during conventional sugar cane processing.

Third Clarification:

Preferably, the juice concentrate is subjected to a further clarifying step 120. This step is identical to clarification step 90. At this step of the process, the juice is preferably maintained at a temperature of approximately 60° C. Following this clarification step, the cane juice concentrate is virtually impurity free; having a purity of approximately 99.9 percent.

Inversion:

Following a final clarification step, the clarified may be subjected to an inversion step, wherein the product is communicated through a series of stainless steel tanks (e.g. three inversion tanks) in order to reduce the pH level of the product to about 4.4 to 4.8, using citric acid, phosphoric acid, or a combination of the two. Furthermore, it is preferred that the temperature is maintained within a temperature range of about 50° C. to 60° C. Once this temperature is reached, an enzyme is added at a rate of at least about 0.11 grams per gallon of product (although a greater amount of enzyme may be added without departing from the intended scope of the invention). For instance, applicant has found success using 0.25 grams of enzyme per gallon of product at 55 degrees Brix. For example, applicant has found success using INVERIME 488 (or, alternatively, INVERZIME 482 and INVERZIME 490), all manufactured by Proenzimas SA of Cali, Columbia. The agitation in the tanks should be constant for a period of about 20 to 30 hours, following a predetermined inversion curve continuously.

Vacuum:

Following clarification step 120, the concentrate, having a Brix of 60 degrees, is subjected to a vacuum step 120 for further product concentration wherein the Brix is increased to approximately 75+/−5 degrees. It will be apparent to those skilled in the art that this step can be performed with a commercially available sugar vacuum pan.

Cooling & Settling:

Following vacuum step 130, the sugarcane juice concentrate is pumped into tank 140 for cooling to a temperature below 54.5° C. The tank is provided with a conical bottom fitted with a small trap for solids. Once the sugarcane concentrate having a Brix of 75+/−5 degrees is adequately cooled, it can be packed for distribution. The resulting product has proven to remain shelf stable for a time period of at least two years.

Referring now primarily to FIG. 1, the following is a list of elements associated with reference numbers that are not included in FIGS. 2 and 3 (Note: FIGS. 2 and 3 pertain to various sub-steps of the process described herein and relating primarily to the method described in applicants prior issued U.S. Pat. No. 6,245,123). The following additional elements are pertinent to the present method, which relates to a modification of the original process in order to preserve policosanols during processing of the raw sugarcane:

| Reference | Process Step/Element |
| --- | --- |
| 101 | Preparation of Talodura Flocculant |
| 102 | Tetrafloc |
| 103 | Acid |
| 104 | Activated Carbon |
| 105 | Steam |
| 106 | Lime |
| 107 | Air |
| 108 | Water |
| 109 | Flocculent |
| 110 | Vacuum |
| 111 | Hot Water |
| 200 | Juice |
| 201 | Cachaza Deposit |
| 112: | Cachaza Disposal Tank |
| 113 | Tetrafloc |
| 114 | Acid |
| 115 | Lime |
| 116 | Hot Water |
| 117 | Flocculent |
| 118 | Activated Carbon |
| 119 | Steam |
| 120 | Air |
| 121 | Solids to Cachaza Tank |
| 122 | Acid and Yeast |
| 123 | Water and Steam |
| 124-126 | Steam |
| 127 | Packaging |

Significantly, some of the modified features and characteristics of the system and method of the present invention have enabled the applicant to achieve a highly-effective, efficient, and cost-effective means for the commercial production of a policosanol-rich version of the sugarcane juice product of the present invention.

For example, the cane should be milled at the lowest possible rate. Furthermore, it is important to cease grinding for at least one hour between the normal production and sugarcane juice concentrate product, in order to enable cleaning of all the tanks and tubes to ensure that there is no contamination of the clean juice with dirty burnt juice residue, and for there to be a reduction in the level of the juice clarifiers.

Maceration:

The cane has to be macerated with clean, preferably treated hot water at a temperature within a range of 80 to 90° C. Applicant has found that the policosanols are precipitated at this temperature. Additionally, emulsifiers or surfactants are added depending upon the variety of cane being processed.

Clarification of the Juice:

The pH level must be maintained within a range of about 7.2 to 7.4, which is a departure from conventional raw sugarcane processing. This is due to the cleanliness of the juice that comes from the mills. Turbidity is the cloudiness or haziness of a fluid caused by large numbers of individual particles that are generally invisible to the naked eye, similar to some in air. The measurement of turbidity is a key test of water quality, or other fluid quality. The propensity of particles to scatter a light beam focused on them is now considered a more meaningful measure of turbidity in water. Turbidity measured this way uses an instrument known in the industry as a nephelometer, with the detector set up to the side of the light beam. More light reaches the detector if there are many small particles scattering the source of the beam than if there are relatively fewer particles. The units of turbidity from a calibrated nephelometer are called Nephelometric Turbidity Units (NTU). To some extent, how much light reflects for a given amount of particulates is dependent upon properties of the particles, such as their shape/geometry, color, and reflectivity. For this reason (and the fact that heavier particles settle quickly and do not contribute to a turbidity reading), a correlation between turbidity and total suspended solids (TSS) is somewhat unusual for each location or situation. In accordance with a preferred implementation of the present process, it is important that the turbidity is maintained at a level less than 80 NTU.

Clarification of the Sugarcane Syrup:

As used herein, the term degrees Brix, represented by the symbol ° bx, is a measurement used to quantify the sugar content of an aqueous solution. More specifically, it is a relative density scale used in the sugar industry to indicate the percentage (%) of cane sugar (sucrose) by weight (i.e. grams of sucrose per 100 milliliters (ml) of solution). After clarification, the clarified juice is passed to the evaporators in order to obtain the cane juice with a degrees Brix (° Bx) value of 55° Bx (+/−5° Bx). It is critical that during the evaporation step the solution never exceeds 90° C., in order to conserve/preserve the aforementioned policosanols.

The resulting syrup should have a pH within a range of about 6.0 and 6.4, and its color, if the prior steps were followed precisely, should not be greater than 4500 IU. The measurement of sugar color is an important function of the laboratories of sugar refineries and raw sugar mills, and is also for users of refined sugar products. For example, the ATM X2 COLORIMETER, manufactured by Index Instruments Limited of Cambridgeshire, England is an instrument dedicated to this important quality control function. The International Commission for Uniform Methods of Sugar Analysis (ICUMSA) recommends the use of 420 nanometers (nm) as the wavelength for color measurements of white and light colored products, and a corresponding wavelength of 560 nm for darker sugars. The result is displayed in ICUMSA Color Units (RI) at the wavelength selected.

In accordance with the method of the present invention, it is preferred that the relative quantities of the various types of flocculants are about twice the quantity typically used. Furthermore, it is crucial that the flow of the clarifiers does not exceed about 20% of the conventional clarifier flow rate, and that in the syrup the tetrafloc is approximately twice the amount conventionally used.

Clarification at Refinery:

In the melting tanks, it is preferable to apply twice the amount of active carbon normally used, in order to decolor to the desired ranges to arrive at a final product with the following characteristics:

Color: 2000 IU
pH Range: 6.2 to 6.4
Turbidity: <1400 IU
Brix: 55° Bx (+/−5° Bx)

This step is critical; it is the final step of filtration, and if done properly, there will not be any problems with the filtration. If filtration is not accurately accomplished, however, the resulting product will have too much color and the filters will rapidly become clogged. Ideally, the sugarcane juice product should exit the clarification step with a bright glow. If this is not the end result, then the turbidity was likely too high and this will likely cause problems with the filters used during subsequent filtration.

Filtration of the Sugarcane Juice Product:

During this stage of the process, it is preferable to incorporate double filtration using so-called Sparkler-type filters. The Initial (First) Filtration is preferably accomplished utilizing a layer of DICTALITE 4187. This results in a filtration of 1 micron. If the previous steps are performed properly, this should result in a flow rate of about 20-2.5 cubic meters of Product per hour, which is very similar to the flow rate of liquor produced at the refinery, albeit maybe 20-30% slower, but otherwise an excellent rate of flow. The target Brix of the syrup being filtered is 55° Bx (+/−5° Bx). A Secondary (Second) Filtration is preferably performed using a new filtering product called ECOSORB S-426, which accomplished all of the beneficial features of DICTALITE product, while enabling further decolorizing via ionic exchange.

Inversion:

Applicant has found great success using a series of three stainless steel inversion tanks, with each of the stainless steel inversion tanks having the capacity to produce five (5) containers at a time. The inversion step must reduce the pH to a level within a range of about 4.4 to 4.8, for example, using citric acid, phosphoric acid, or a combination of the two. Furthermore, the target temperature should be maintained within a range of about 50° C. to 60° C. Once the target temperature has been achieved, enzyme is added, preferably in a quantity of 0.11 grams per gallon of sugarcane juice concentrate at 55 degrees Brix. By way of example, the present applicant has found success using an enzyme sold under the tradename INVERZIME 488 (or, alternatively, INVERZIME 482 and INVERZIME 490), all of which are manufactured by Proenzimas SA of Cali, Columbia.

Juice Product Concentration:

Significantly, through extensive experimentation, the present applicant has discovered that it is crucial that the temperature of the sugarcane juice product never exceeds 90° C. throughout the entire process, in order to ensure maximized preservation of the natural sugarcane policosanols, as previously mentioned herein. Through extensive trial-and-error, applicant has determined that exceeding this 90° C. temperature causes burning of the product and, significantly, a corresponding loss of policosanols in the product. Again, applicant has determined that the ideal Brix for the syrup form of the policosanol-rich sugarcane-based product produced in accordance with the present method is 75+/−5 degrees Brix.

Referring now particularly to FIGS. 4A through 4D, an alternative implementation of the system of the present invention similar to that initially introduced in FIGS. 1-3, but illustrating the incorporation of highly-beneficial preferred surfactant and emulsifier introduction sites, resulting in an improved product quality and improved sugarcane product policosanol content, is presented.

Figure 4A:
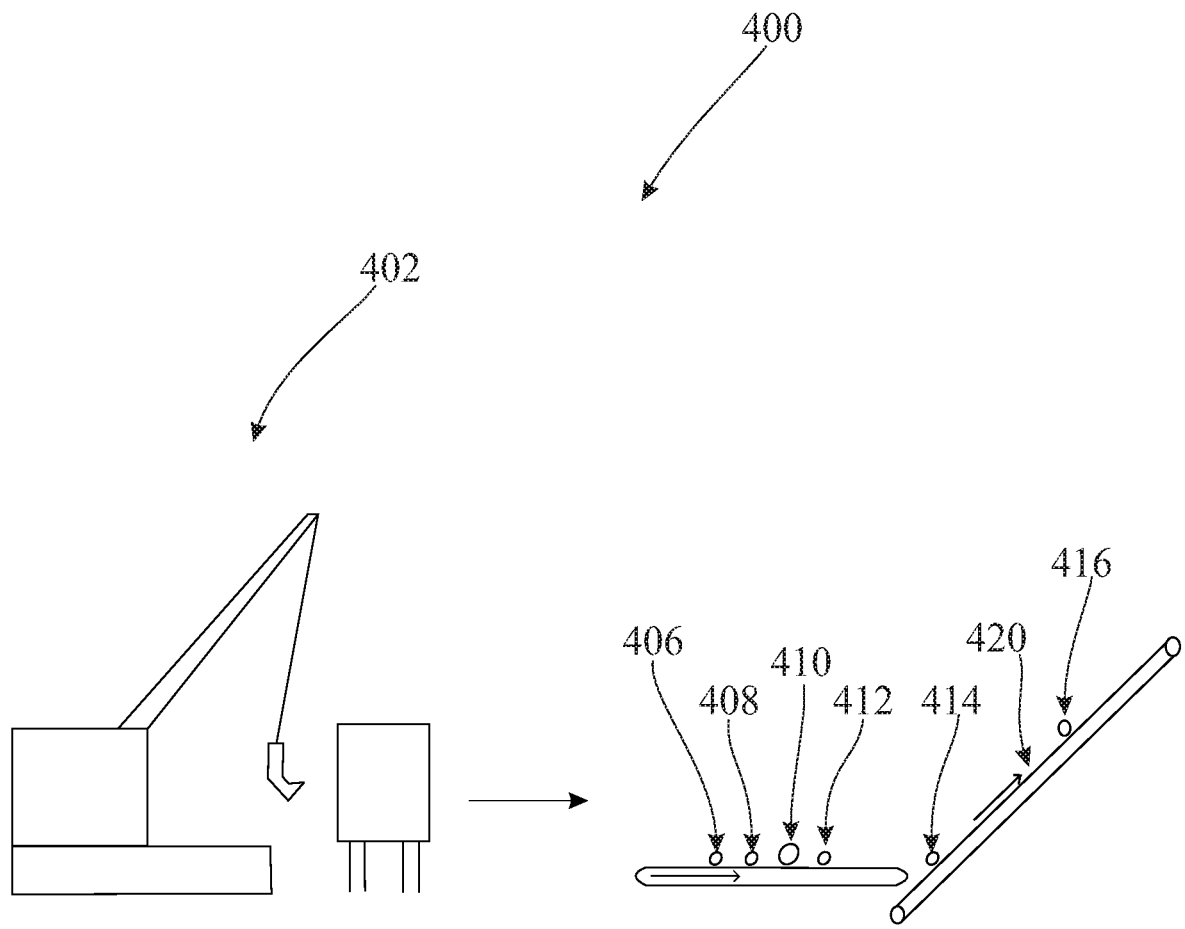
FIGS. 4A through 4D are a schematic illustration of an exemplary system/method for producing a consumable policosanol-rich sugarcane-based product, illustrating the addition of surfactants and emulsifiers at particular locations during processing of the raw sugarcane in order to further maximize the relative amount of policosanols in the final product, in accordance with an alternative implementation of the present invention.

Referring initially to FIG. 4A, an initial sub-component of the system is shown, including equipment, such as cranes and transportation vehicles shown generally as reference numeral 402. As previously described hereinabove, preselected sugarcane sticks having high Brix, 18+/−10 and policosanol content are introduced to an initial shredded cane conveyor/conductor, represented generally as reference numeral 404. Conveyor 404 may include a first leveling roller 406, a sugarcane stick shredding apparatus 408, a feeding drum 410, and a cane defibrillation apparatus 412. The shredded cane may be subsequently transferred to a second, adjacent shredded cane conductor/conveyor 420, which may include a second leveling roller 414 and a third leveling roller 416. The system is continued in FIG. B, in which the second conductor/conveyor 420 has been reproduced for clarity.

Figure 4B:
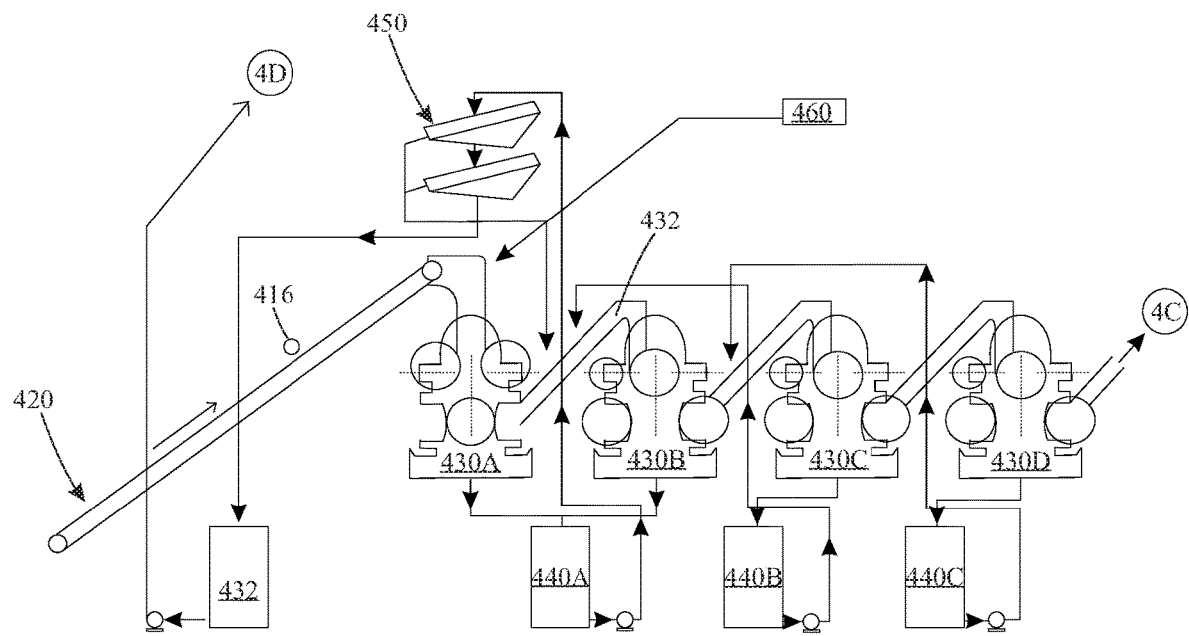

Referring now to FIG. 4B, the shredded sugarcane is processed through the entire series of roller mills, denoted 430A through 430F, which function in conjunction with tanks 440A through 440E, in a manner as previously described hereinabove with regard to FIG. 2. Furthermore, a microscopic bagasse processing system portion, represented by reference numeral 450, is in communication with diluted juice product tank 432. As indicated in FIG. 2 for clarity, diluted juice product from tank 432 is communicated to heaters 478 (FIG. 4D). Likewise, as further indicated in FIG. 2, juice product from fourth roller mill 430D is communicated to fifth roller mill 430E (FIG. 4C).

Figure 4C:
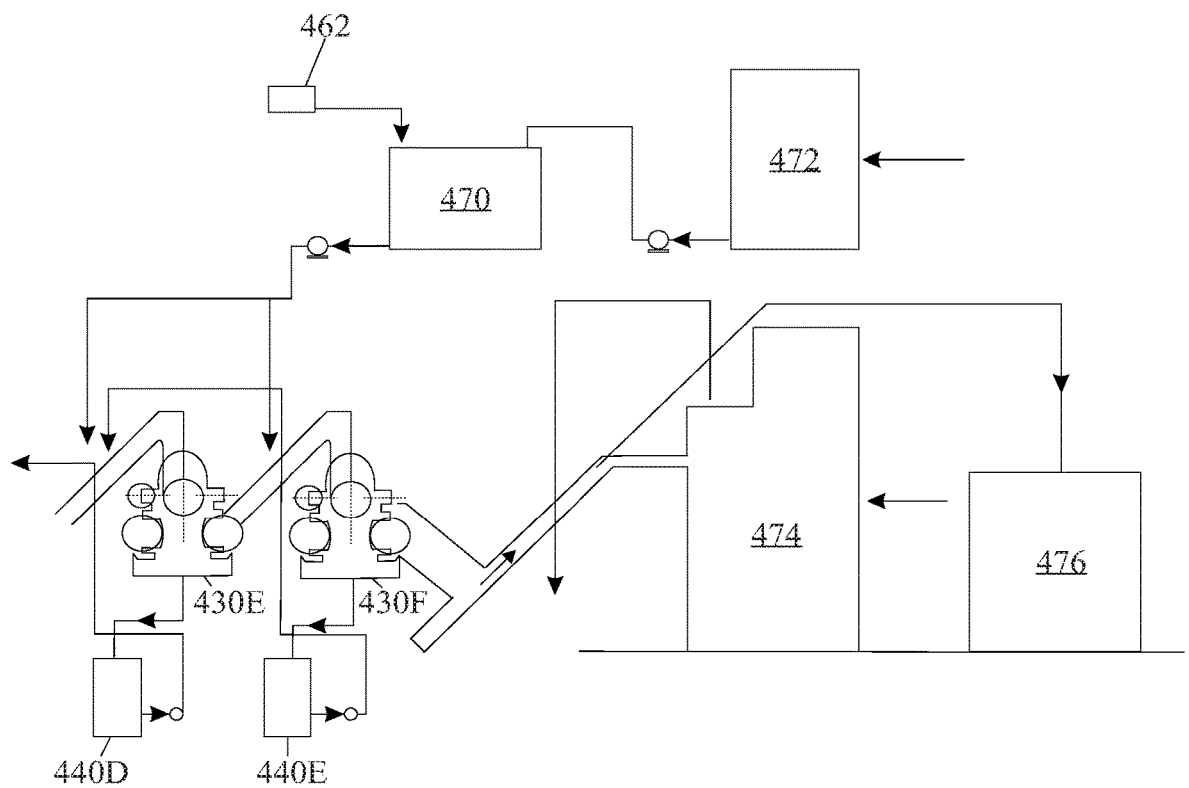
Figure 4D:
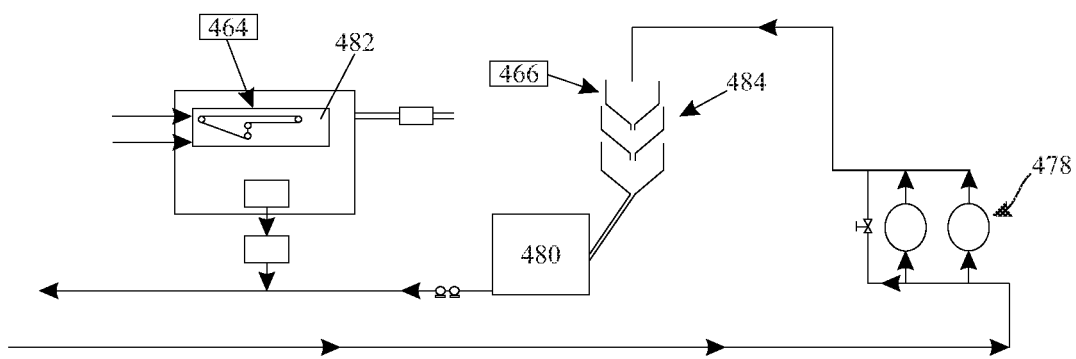

Referring now to FIG. 4C, system boilers are represented by reference numeral 474, and a bagasse storage represented by reference numeral 476. Furthermore, a condenser tank is represented by reference numeral 472, and a maceration tank is represented by reference numeral 470. The function and purpose of the aforementioned components is as previously described hereinabove with regard to FIG. 2. Significantly, for reasons described hereinbelow, a quantity of emulsification product (50 ppm to 1,500 ppm, depending upon the variety of the cane)—represented by reference numeral 462—is preferably introduced into maceration tank 470.

Referring now to FIG. 4D, a quantity of surfactant (50 ppm to 1,500 ppm, depending upon the variety of the cane), represented by reference numeral 466 and second quantity of surfactant (100 ppm), represented by reference numeral 464, is introduced into the system as shown.

Significantly, during the process of obtaining sugarcane juice concentrate product it is crucial to add quantities of emulsifier and surfactant products at particular locations during the process, as these help to reduce the viscosity and precipitate the waxes and gums of the sugarcane, which contain policosanols that have not been extracted and precipitated into the juice by mechanical means during the process. In particular, a surfactant (50 ppm to 1,500 ppm, depending upon the variety of the cane) is added before the first roller mill 430A and to the band filter 482 of the cachaza. Likewise, an emulsifier (50 ppm to 1,500 ppm, depending upon the variety of the cane) is added before the fifth and sixth roller mills, 430E and 430F, respectively, just prior to the juice clarification process, and just prior to the fifth and sixth roller mills of the molasses clarification. The emulsifier or surfactant is provided at 50 ppm to 1,500 ppm, depending upon the variety of the cane.

Significantly, the juice product of the present invention may be produced in a variety of forms including, but not limited to, a juice beverage and a juice concentration, for example, in the form of a sweetening agent. Furthermore, the juice product extracted by the rolling mills 440A through 440E, prior to being subjected to any clarification steps, incorporates a policosanol-rich composition that may be used in the form of both a juice beverage and a concentrated juice sweetening agent that may be added to any of a variety of existing liquid beverages.

Juice product extracted from the mills following clarification incorporates a policosanol-rich composition that may be used in the form of both a juice beverage and a concentrated juice sweetening agent that may be added to any of a variety of existing liquid beverages.

Juice product extracted from the mills following clarification and evaporation concentrated juice product) incorporates a policosanol-rich composition that may be used in the form of both a juice beverage and a concentrated juice sweetening agent that may be added to any of a variety of existing liquid beverages, and has a shelf life of approximately one month.

Furthermore, applicant has found that an extracted concentrated form of the juice product, after being subjected to clarification, filtration, evaporation, and inversion steps of the present method has a shelf life of at least approximately two years.

Significantly, applicant has discovered that the method of the present invention not only preserves naturally-occurring policosanols from the raw sugarcane but also preserves all of the major (i.e. macro-, micro-, and nano-) nutrients from the raw sugarcane. Accordingly, applicant's method may be incorporated for the large-scale commercial production of sugarcane-based policosanol-rich and nutrient-rich beverages, beverage concentrates (e.g. for use as sweetening agents and the like), which provide the aforementioned cholesterol-reducing and other health benefits commonly associated with expensive pharmaceutical products, at a fraction of the cost while eliminating a host of harmful side effects commonly associated with statins and other cholesterol-reducing drugs. As a result, applicant's method is highly beneficial in that it offers a means for enabling the treatment of high cholesterol and related health risks to potentially tens of millions of individuals around the world whom, otherwise, would have no means for seeking help via the conventional healthcare industry.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as described in the claims.

What is claimed is:

1. A method for processing a quantity of raw, unwashed sugarcane sticks to produce a policosanol-rich sugarcane juice product via a sugarcane juice product processing system, comprising steps of:
    shredding the unwashed sugarcane sticks and conveying the shredded and unwashed sugarcane sticks toward a first one of a series of mechanical roller mills;
    contacting the conveyed sugarcane sticks with a quantity of a surfactant prior to the sugarcane sticks reaching said first one of the series of mechanical roller mills;
    extracting sugarcane juice from the unwashed, shredded sugarcane sticks via the series of roller mills, the shredded sugarcane sticks, while being conveyed through the series of roller mills, macerated with water having a temperature maintained within a range of 80° C. to 90° C. to produce a volume of water-diluted extracted sugarcane juice product;
    filtering the diluted extracted sugarcane juice product through at least one filter;
    stabilizing the pH of the extracted and filtered sugarcane juice in a non-acidic solution of calcium hydroxide to a stabilized pH level within a pH range of 7.2 to 7.6;
    heating the pH-stabilized sugarcane juice to a temperature within a range of 80° C. to 90° C.;
    clarifying the heated and pH-stabilized sugarcane juice, wherein the heated and pH-stabilized sugarcane juice is flocculated using a mixture of water and at least one flocculate product, the flocculated sugarcane juice forming a glutinous froth, the glutinous froth retained and subjected to further processing in order to preserve a rich concentration of policosanols contained therein, the policosanol-rich processed froth subsequently reintroduced into the sugarcane juice product being processed;
    evaporating the clarified sugarcane juice product via an evaporation apparatus including a series of evaporators, thereby incrementally increasing a sugar and policosanol concentration of the sugarcane juice product to create a post-evaporation, policosanol-rich concentrated sugarcane juice syrup having a desired post-evaporation Brix value, wherein the Brix value of the sugarcane juice product is maintained at or below 70° Bx during the entire evaporation step; and
    extracting the evaporated sugarcane juice concentrate from the evaporation apparatus at said desired post-evaporation Brix value,
    wherein the sugarcane processing method maintains a juice product temperature at or below 90° C. throughout said process to prevent evaporation of policosanols therefrom.

2. The method recited in claim 1, wherein the step of evaporating the flocculated sugarcane juice further comprises increasing a concentration of said sugarcane juice product to create a post-evaporation, policosanol-rich concentrated sugarcane juice syrup having a desired Brix value within a range of 50° Bx to 60° Bx.

3. The method recited in claim 1, wherein said further processing of the glutinous froth comprises a step of subjecting the glutinous froth to vacuum press filtration via a vacuum belt filter press.

4. The method recited in claim 1, further comprising, after the step of extracting the evaporated sugarcane juice concentrate, steps of:
    introducing the extracted evaporated sugarcane juice concentrate to a vacuum pan to further concentrate the sugarcane juice concentrate to a Brix within a range of 70° Bx to 80° Bx; and
    cooling the vacuum-concentrated sugarcane juice concentrate to a temperature below 54.5° C.

5. The method recited in claim 1, wherein the step of filtering the diluted extracted sugarcane juice product further comprises filtering sugarcane juice extracted from a first pair of said series of roller mills.

6. The method recited in claim 3, wherein the step of further processing of the retained glutinous froth further comprises, prior to subjecting the glutinous froth to vacuum filtration, a step of heating the retained glutinous froth for at least one hour.

7. The method recited in claim 1, wherein the step of stabilizing the pH of the sugarcane juice further comprises stabilizing the pH of the sugarcane juice to a pH within a range of 7.4 to 7.6.

8. The method recited in claim 1, wherein the step of extracting the sugarcane juice concentrate from the evaporation apparatus at a desired degrees Brix value further comprises extracting the sugarcane juice concentrate from the evaporation apparatus at a post-evaporation sugarcane juice product concentration having a Brix of about 60 degrees.

9. The method recited in claim 1, wherein said at least one flocculate product further comprises a natural flocculate.

10. The method recited in claim 1, further comprising a step of subjecting the extracted sugarcane juice product concentrate to vacuum until the Brix value of the concentrate is increased to a Brix value within a range of 70 to 80 degrees Brix.

11. The method recited in claim 1, further comprising, following a step of final clarification, a step of subjecting the juice product to an inversion process, wherein, prior to said inversion process, the sugarcane juice is in a condition adequate for use as at least one of: a packaged potable drinking juice product and a sugarcane juice component of a sweetening agent.

12. The method recited in claim 11, wherein the step of inversion further comprises steps of:
communicating the clarified juice product through a series of stainless steel inversion tanks to effectively reduce the pH level of the juice product using at least one of: citric acid, phosphoric acid, and a combination of citric acid and phosphoric acid.

13. The method recited in claim 12, wherein the step of inversion further comprises steps of:
adding a quantity of an enzyme to the concentrated sugarcane juice product to reduce a pH level of the product to a pH value within a range of 4.4 to 4.8; and
maintaining a temperature of the juice product within a temperature range of 50° C. to 60° C.

14. The method recited in claim 1, further comprising a step of producing a policosanol-rich sugarcane juice-based product, the policosanol-rich sugarcane juice-based product comprising at least one of: a non-concentrated policosanol-rich drinking beverage; a semi-concentrated, policosanol-rich sugarcane juice-based product adapted for use as a sweetening additive; and a highly-concentrated, policosanol-rich sugarcane juice-based nutraceutical.

15. The method recited in claim 1, wherein the step of clarifying the heated and pH-stabilized sugarcane juice further comprises a step of adding a volume of an emulsification product to the heated and pH-stabilized sugarcane juice product.

16. The method recited in claim 1, wherein the step of evaporating the clarified sugarcane juice product via an evaporation apparatus further comprises a step of adding a volume of an emulsification product to the clarified sugarcane juice product.

17. The method recited in claim 3, further comprising a step of adding a volume of an emulsification product to the glutinous froth being subjected to the vacuum belt filter press.

18. The method recited in claim 14, further comprising a step of packaging the policosanol-rich sugarcane juice-based product.

* * * * *